United States Patent [19]

Anderson et al.

[11] Patent Number: 5,452,714
[45] Date of Patent: Sep. 26, 1995

[54] HUMAN LUNG VENTILATOR SYSTEM

[75] Inventors: Ralph Anderson, Carlsbad; Nurit Yehushua; Paul Smargiassi, both of San Diego; Paul Thompson, Santee; Fred Moore, Newbury Park, all of Calif.

[73] Assignee: Infrasonics, Inc., San Diego, Calif.

[21] Appl. No.: 67,141

[22] Filed: May 26, 1993

Related U.S. Application Data

[63] Continuation of Ser. No. 535,191, Jun. 7, 1990, Pat. No. 5,237,987.

[51] Int. Cl.$^6$ .................................................. A62B 7/00
[52] U.S. Cl. ................................. 128/205.11; 128/204.21
[58] Field of Search ........................ 128/204.18, 205.11, 128/205.24, 204.21

[56] References Cited

U.S. PATENT DOCUMENTS

| | | | |
|---|---|---|---|
| 2,080,272 | 5/1937 | Hollman | 251/208 |
| 2,247,227 | 6/1941 | Findley | 251/208 |
| 3,092,142 | 6/1963 | Willson | 137/614.11 |
| 3,626,755 | 12/1971 | Rudolph | 128/725 |
| 3,848,617 | 11/1974 | Dray | 137/88 |
| 4,023,587 | 5/1977 | Dobritz | 137/88 |
| 4,072,148 | 2/1978 | Munson et al. | 128/205.11 |
| 4,076,021 | 2/1978 | Thompson | 128/205.18 |
| 4,150,670 | 4/1979 | Jewett et al. | 128/204.22 |
| 4,201,517 | 5/1980 | Ferguson | 417/26 |
| 4,204,536 | 5/1980 | Albarda | 128/204.22 |
| 4,345,612 | 8/1982 | Koni et al. | 137/101.19 |
| 4,587,967 | 5/1986 | Chu et al. | 128/204.21 |
| 4,602,653 | 7/1986 | Ruiz-Vela et al. | 137/88 |
| 4,727,871 | 3/1988 | Smargiassi et al. | 128/205.12 |
| 4,763,692 | 8/1988 | Bachman et al. | 137/625.3 |
| 4,821,709 | 4/1989 | Jensen | 128/204.21 |
| 4,867,152 | 9/1989 | Kou et al. | 128/204.21 |
| 4,957,107 | 9/1990 | Sipin | 128/204.21 |
| 4,984,158 | 1/1991 | Hillsman | 128/725 |
| 5,237,987 | 8/1993 | Anderson et al. | 128/204.18 |

*Primary Examiner*—Edgar S. Burr
*Assistant Examiner*—Aaron J. Lewis
*Attorney, Agent, or Firm*—Gregory Garmong

[57] ABSTRACT

A patient ventilator system provides a controllable flow and volume of a mixed inhalation gas to a patient, and receives exhaled gas from the patient. The ventilator system includes gas flow controllers that mix air and oxygen, and provide the mixture to the patient with a controllable inhalation cycle. The ventilator system monitors the resulting patient pressures and volume of gas exhaled by the patient, as necessary. Compressed air is provided to the gas controller in the event of an absence of an external gas supply by a compressor. A controller permits the user of the ventilator system to control ventilation mode, gas pressure, composition, and flow rate of the mixed gas with a single control knob.

12 Claims, 10 Drawing Sheets

HUMAN LUNG VENTILATOR SYSTEM

This is a continuation, of application Ser. No. 07/535,191, filed Jun. 7, 1990, now U.S. Pat. No. 5,237,987.

BACKGROUND OF THE INVENTION

This invention relates to apparatus for assisting or forcing a person to breathe, and, more particularly, to a ventilator system that is flexible in operation and easily controlled by a user.

In many cases the discomfort of critically ill persons can be eased, and their recovery hastened, by a proper program of breathing assistance supplied by a device termed a "ventilator". In simplest terms, the ventilator either forces pressurized gas into the lungs (e.g., a positive-pressure ventilator) or expands the chest cavity of the patient to draw gas into the lungs (e.g., a negative-pressure ventilator) under a selectable schedule of gas composition, pressure, and flow pattern. While negative-pressure ventilators enjoyed a degree of popularity in the past, their use has been largely replaced by positive-pressure ventilators, and the present invention relates to such positive-pressure ventilators.

The ventilator typically includes a compressor that supplies pressurized air, or the ventilator may operate from hospital pressurized air and oxygen lines. The gas is provided to the patient for inhalation according to a prescribed schedule, such as, for example, a specific pressure profile or a specific gas volume delivery profile with time. The inhalation gas flows to the patient and into the lungs. Many ventilators can be adjusted to either force breaths or respond only to the patient's attempts to breathe and assist in that breathing, or operate in some more complex pattern.

The exhaled gas that flows from the patient may also be controlled. For example, in some cases it has been found useful to maintain the exhaled gas under positive pressure, and the ventilator provides a positive end expiratory pressure (PEEP) mechanism for that purpose. A conventional PEEP mechanism restricts exhalation by closing off the path for exhaled gas flow when airway pressure drops below the pre-set PEEP level.

A primary consideration in the design of ventilators is safety, in terms of both avoiding adverse effects of apparatus failure and ensuring that the ventilator aids the patient's own efforts to breath. The ventilator must cooperate with the efforts of the patient to breathe, and indeed the ventilator must permit the patient to be "weaned" from full ventilator dependence to self sufficiency. Ideally, the ventilator should never work against the patient's own efforts. Instead, the ventilator may provide aid for patient-induced breaths, may induce ventilation without the assistance of the patient, or may accomplish a combination schedule of permitting or assisting the patient with self-triggered breaths and then ventilating without patient assistance between the patient's own breaths.

Respiratory therapy has developed into a complex field as more has been learned about the beneficial effects of proper ventilation in a variety of circumstances. Doctors are trained to understand the requirements of proper gas supply to the lungs, and to determine a proper schedule of patient ventilation that is preferred in particular types of cases. For example, the patient with emphysema normally requires quite a different ventilation schedule than the patient recovering from chest surgery.

Early ventilators used all-pneumatic systems for control of gas flow, gas blending, breath rates, patient breath assistance, and pressure control. These systems provided little monitored data and few (or no) alarms and therefore relied heavily on the skill and diligence of the operator to establish and maintain ventilation parameters. Later generations of ventilators contained electronic circuits which provided more precise control of timing parameters such as breathing rates and inspiratory time, and had pressure and flow measuring devices to provide displays of monitored data and to facilitate alarm activations if patient airway pressures, breath-to-breath gas volumes, or frequency of breaths were outside of user-established limits.

The current generation of ventilators use microprocessors to control most of the parameters of ventilation and contain pressure and flow measurement transducers which provide electrical data (via analog-to-digital converters) to the microprocessors for display of monitored parameters and for alarm activations. These microprocessor based ventilators, as compared to previous generations, may have improved flow and pressure control accuracy, may display data in graphic form and present additional data based upon mathematical manipulations of pressure and flow data, and may offer improved safety features. A main advantage of microprocessor based ventilators is the ability to add new features by changing only the memory integrated circuits (usually EPROMs) containing the software programs.

One major disadvantage of some current designs of microprocessor based ventilators is the complexity of the user interface. Typically, ventilator parameters are either input by control knobs, with one knob for each parameter setting as in the prior electro-mechanical ventilators, or by keyboard entry. Parameter settings are typically displayed on seven-segment type displays, either continuously, upon selection, or sequentially in ticker-tape fashion. Likewise, monitored data is displayed on seven-segment type displays. Because of space limitations on the control panel, not all monitored data can be displayed at the same time, and the desired data must be selected for display by selection switches.

As new features and new ventilating modes are added, the complexity of operation increases because the existing controls and display areas must be burdened with the requirement of facilitating input and display of the new features. The microprocessor controlled ventilator also tends to be more costly than previous generations because of the need for designing unique pneumatic control and monitoring devices which are controllable by the microprocessor as well as the need for a non-volatile memory for storage of ventilation parameter and alarm threshold settings. The exhaled gas measurement transducer as an example has traditionally been difficult to design and very expensive to build because of the requirements of accurate flow measurement with very small pressure drops.

Another problem with microprocessor based systems is their susceptibility to AC power line noise. Voltage spikes and other forms of electrical noise can pass through conventional power supplies and interfere with the microprocessor's ability to access the program code from ROM memory and in reading and writing of data to RAM memory. Momentary drop-outs of power line voltage can cause the ventilator power supply's regulated voltages to drop below the operating limits of the integrated circuits, with unpredictable consequences. Power supplies for microprocessor based ventilators must therefore be designed to be immune to all forms of power line noise. Such immunity is normally accomplished with elaborate line voltage spike suppressors and EMI filters.

Conventional ventilators are without battery back-up power supplies and therefore must be designed to shut down in a safe manner with alarms activated if the line voltage momentarily drops below acceptable limits. These requirements are difficult to achieve, and it is nearly impossible to verify that the system is immune to all forms of electrical noise and all durations of power line drop-outs. Hospital power is always backed up by a motor-generator which starts up when the power line drops out. The switch-over in power sources which occurs during a power line blackout or brownout can cause momentary voltage dropouts, voltage spikes, power line frequency shifts, etc., which in turn can cause microprocessor (and other electronic) based systems to fail or shut down. In addition, occasionally the back-up power systems themselves fail, causing all electronic systems in the hospital which are not battery backed to shut off, thereby causing a hazardous situation for the patients.

Thus, there is a continuing need for a ventilator system that is easier for hospital personnel to use, less expensive, and more tolerant of fault situations such as powerline problems. The ventilator must be a readily controlled, convenient apparatus that supplies the required ventilation conditions with minimal chances of error, either in setting the ventilation conditions or in meeting the set schedule. The present invention fulfills this need, and further provides related advantages.

SUMMARY OF THE INVENTION

The present invention provides a ventilator system that is exceptionally convenient to use, and is precisely controllable to permit a selected ventilation schedule to be provided to the patient. Flexibility and precision are included in the operation of the ventilator system, with careful engineering to reduce the costs of the apparatus as much as possible consistent with the overriding concern for patient safety. The apparatus provides a compact unit that is well suited for hospital or other patient-care environments.

In accordance with the invention, a ventilator system for use in assisting a patient to breathe comprises gas control means for mixing and regulating the gas that is to flow to a patient and receiving the gas that flows from the patient; and controller means for controlling the gas control means, the controller means including a single knob that controls ventilation mode, gas pressure, gas composition, and flow rate of the gas that flows to the patient.

In another aspect of the invention, a ventilator system for use in assisting a patient to breathe comprises gas control means for mixing and regulating the gas that is to flow to a patient and receiving the gas that flows from the patient, the gas control means including flow control means for mixing together controllable amounts of two gases to form a mixed gas that flows to the patient, the flow control means including a custom-calibrated rotary flow control valve for each of the two gases; and controller means for controlling the gas control means.

In a preferred approach, the inhalation flow schedule of gas pressure, flow, and composition as a function of time is determined by a pressurization/flow controller that receives pressurized gas of essentially constant pressure, either from a compressor or from an external source. Two (or more) gases, typically air and oxygen, are mixed together to form a mixed gas composition that is supplied to the patient. The amount of each gas and its flow rate as a function of time are established by an open loop gas control system using controllable stepper-motor-driven rotary flow control valves that are individually calibrated and periodically zeroed during operation. This system has the advantage that it is simpler than closed loop systems. The flow rate of the mixed gas is determined by measuring the pressure drop across an adjustable gas orifice, which is more readily and accurately accomplished than a direct flow rate measurement.

The inhalation gas mixture then is conducted to the patient, first passing through a conventional bacteria filter and humidifier. A nebulizer subsystem supplies medication to the gas mixture upon demand.

Exhaled gas from the patient passes through a tube to a filter. A water trap serves as a drain and reservoir for moisture condensed in the tubing. Alternatively, the tubing may be heated to prevent condensation. The pressure of the exhaled gas is controllable with a positive end expiratory pressure (PEEP) subsystem that applies a selectable pressure profile to the exhaled gas.

In some situations a supply of filtered compressed air is not available, and the ventilator system includes a compressor that provides such a supply. Since the ventilator system is normally operated in the room of a sick or injured person, an important virtue is quiet operation. A shortcoming of many prior ventilator compressors is that they generate excessive noise because they operate continuously at maximum output flow rate and pressure. More over, continuous-operation compressors must be sized for maximum gas flow rates. The present compressor motor runs constantly, with valves to alternately fill an accumulator and then idle, pumping against no load. The accumulator in turn supplies gas to the pressurization/flow controller. The compressor may therefore be provided in a smaller, quieter size and structure than with a non-cycling compressor.

Conventional ventilator controllers utilize an array of separate control switches and knobs to set the gas flow schedule, flow rates, pressures, PEEP schedule, and other control parameters. The myriad of controls can be confusing to even a well-trained operator, particularly in the circumstances of a critical patient situation. The present controller utilizes microcomputer-based window and menu manipulation software to permit all significant control functions to be determined with a single control knob. The control parameters, status alarms, and monitored date are displayed on a clearly delineated cathode ray tube (CRT) monitor screen so that the operator can see the current status and how that status is to be affected by any particular adjustment.

The present invention therefore provides an important advance in the art of ventilator technology, both in ventilator operation and in ventilator control. The unit is simple to operate with a single knob that enters all command functions. On-screen information presents all command, data, and alarm information, and even displays prompt and assistance information to the user. Low-cost metering valves are precise, yet readily calibrated and controlled. A plurality of microprocessors are used to achieve wide flexibility in system functions. The electronics operates from a battery that is continuously charged when line voltage is available, and the battery filters noise from the power signal so that it does not reach the electronics. The improved apparatus is economically competitive with conventional apparatus, and has improved safety, ease of use, and reduced noise. Other features of the present invention will be apparent from the following detailed description of the preferred embodiment, taken in conjunction with the accompanying drawings, which illustrate, by way of example, the principles of the invention.

DETAILED DESCRIPTION OF THE PREFERRED EMBODIMENT

The preferred embodiment resides in a ventilator system used to assist a patient to breathe. The structure of the ventilator system as a whole is illustrated in FIG. 1, and FIGS. 2–11 illustrate the details of various subsystems.

In accordance with a preferred embodiment of the invention, a ventilator system for use in assisting a patient to breathe comprises gas control means for mixing and regulating the gas that is to flow to a patient and receiving the gas that flows from the patient, the gas control means including flow control means for mixing together controllable amounts of two gases to form a mixed gas that flows to the patient, the flow control means including a custom-calibrated rotary flow control valve for each of the two gases, an inhalation flow sensor through which the mixed gas flows, the inhalation flow sensor including a screen through which the mixed gas flows and a pressure sensor that senses the pressure drop across the screen, whereby the mixed gas flow rate is determined with a preexisting calibration relationship, a nebulizer that injects a controllable flow of a third component into the mixed gas stream, ventilation tube means extending to the patient for conducting the mixed gas to the patient and for receiving exhaled gas from the patient, the ventilation tube means including a filter for the mixed gas, a humidifier for the mixed gas, a water trap for the exhaled gas, and a filter for the exhaled gas, and positive end expiration pressure means for controllably pressurizing the exhaled gas; compressor means for supplying compressed gas to the gas control means, in the event that an external supply of compressed gas is not available, the compressor means including a compressor that operates continuously against a compressor accumulator and is sized to meet average rather than peak gas flow volume; and controller means for controlling the gas control means and the compressor means, the controller means permitting the setting of ventilation mode, gas pressure, gas composition, and flow rate of the mixed gas with a single control knob.

Figure 1:
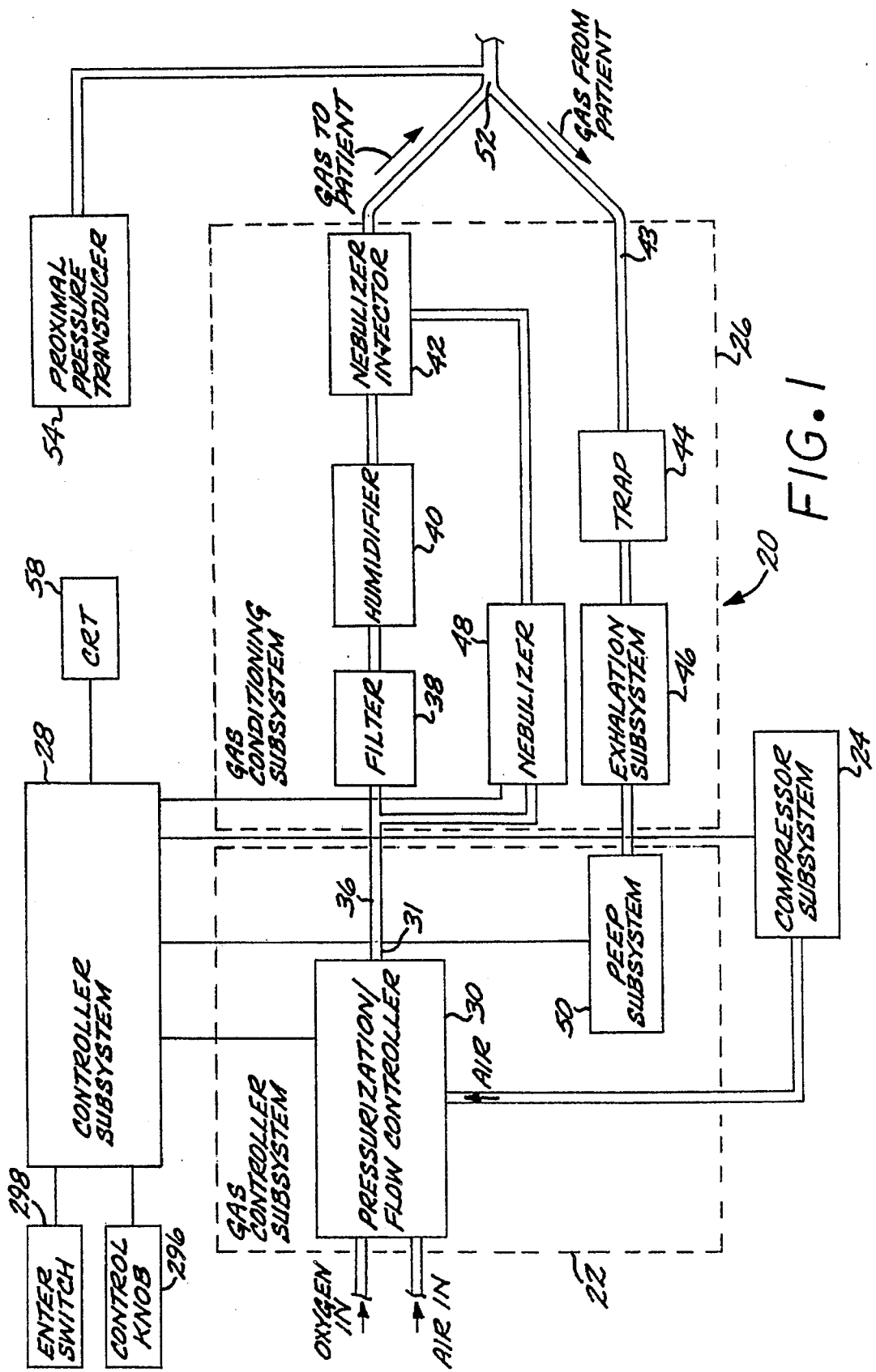
FIG. 1 is a block diagram of the overall arrangement of the ventilator system.

Referring to FIG. 1, a ventilator system 20 includes a gas controller subsystem 22 that supplies a controlled flow of inhaled gas to the patient and also controls the pressure of the exhaled gas, a compressor subsystem 24 that supplies pressurized gas to the gas controller subsystem 22, a gas conditioner subsystem 25 that alters the composition of the gas flows by filtering, humidifying, dehumidifying, and as otherwise required, and a controller subsystem 28 that controls the operation of the other components.

The gas control subsystem 22 includes a pressurization/flow controller 30 that is supplied with pressurized oxygen from an external pressurized oxygen source 32, and with pressurized air from an external pressurized air source 34 or the compressor subsystem 24. The oxygen and air supplied to the gas control subsystem 22 preferably have a pressure of from about 30 to about 90 psig (pounds per square inch, gauge). The gas control subsystem 22 regulates the pressure of the oxygen and air, and then mixes them according to the commands received from the controller subsystem 28, in a manner to be described in detail subsequently. The resulting mixed gas flow 35 has a particular composition, flow rate, and pressure profile precisely determined according to the controller subsystem commands.

The mixed gas flow 36 passes to the gas conditioner subsystem 26 through a manifold 31, prior to reaching the patient for inhalation. The gas conditioner subsystem 26 alters the composition of the gas stream, not with respect to the oxygen and air content, but instead with respect to other components that are desirably or undesirably present. A filter 38 removes microscopic particles such as bacteria from the gas flow 36 that might adversely affect the patient. A humidifier 40 adds moisture to the gas flow 36, as might be required for a particular patient, and particularly when the atmospheric humidity is low. A nebulizer injector 42 and its associated nebulizer 48 add medication, such as for example a decongestant, to the gas flow 36.

A stream of exhaled gas 43 from the patient is also processed through the gas conditioner subsystem 26. The exhaled gas is passed through a water trap 44 to remove excess moisture and through an exhalation subsystem 46, to be described in more detail subsequently, that includes a filter for the exhaled gas and a gas flow monitor.

The filter 38, humidifier 40, nebulizer injector 42, trap 44, and tubing that forms the Y leading to and from the patient are all commercially available products, and are well known in the art.

A PEEP subsystem 50, which is part of the gas controller subsystem 22, controls the pressure in the airway during expiration. The PEEP (positive end expiratory pressure) subsystem 50 prevents the pressure in an airway 52 from falling below some preselected minimum value during exhalation, so that a positive pressure is retained in the lungs at the conclusion of the expiration of air. A doctor may choose such therapy for a variety of reasons, such as to prevent collapse of the alveoli of the lungs during exhalation.

Pressure in the airway 52 is measured by a proximal air pressure sensor 54 at a point near the Y of the tube extending to the patient.

Figure 2:
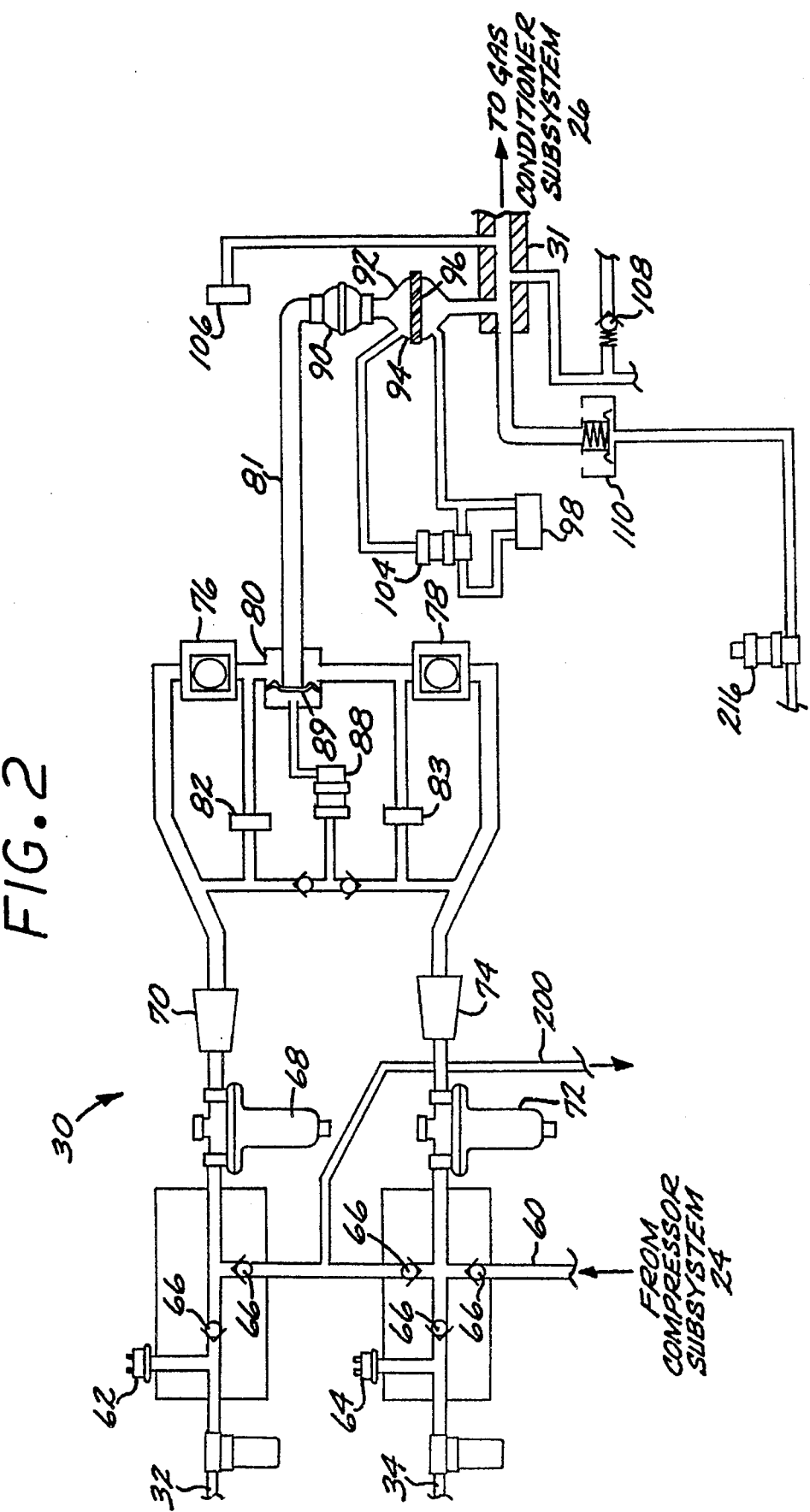
FIG. 2 is a block diagram of the pressurization/flow controller subsystem.

FIG. 2 illustrates the pressurization/flow controller 30 in greater detail. Oxygen is provided to the system through the oxygen source 32, and air is provided either from the air source 34 or a line 60 from the compressor subsystem 24. The pressure in the oxygen side of the gas supply is sensed by an oxygen pressure sensor 62, and the pressure in the air side of the gas supply is sensed by an air pressure sensor 64. Check valves 66 prevent gas flow in the directions that, but for the check valves 66, would result in possible contamination of the gas supplies by the other gas.

The oxygen passes through a regulator 68 wherein its pressure is controlled to the range of about 6½ to 7½ pounds per square inch, gauge (psig) and then through a filter 70 having a filter element that removes particles of less than about 0.3 micrometers. Similarly, the air passes through a regulator 72 and filter 74 that operate identically.

The flow rate of oxygen is established by a rotary valve 76, and the flow rate of air is established by a rotary valve 78. These valves provide the basic control function for the gas flows to the patient, and their construction will be discussed in more detail subsequently. The gas outflows from the valves 76 and 78 are mixed and provided to an outflow line 81.

The pressure drop across the oxygen rotary valve 76 is measured by an oxygen pressure drop transducer 82, and the pressure drop across the air rotary valve 78 is measured by an air pressure drop transducer 83. The pressure drop in each case is a function of upstream pressure and flow rate through the valve. Pressure drops outside of established limits indicate a malfunction of the valves 76 and 78, if such should occur.

In the event of a malfunction of one of the valves 76 or 78, a valve 88 is operated to permit a direct flow of gas into a stop valve 80 and pressurize a diaphragm 89 therein. The diaphragm flexes to the right in the view of FIG. 2, closing the outflow line 81. There is no gas flow through the outflow line 81 to the patient. This safety mechanism prevents the full force of the inlet gas being applied to the patient's lungs.

The mixed gas in the line 81 is filtered in a filter 90 having a filter that removes particles of less than about 0.3 micrometer size.

The flow rate of the mixed gas is sensed in a flow rate sensor 92. The gas flows through a sensor body 94 having a wire mesh screen 96 therein, through which the gas must flow. The pressure of the gas drops slightly as it passes through the screen 96, the pressure drop being a function of the flow rate of the gas. That pressure drop across the screen 96 is sensed by a pressure transducer 98, whose reading is therefore indicative of the flow rate of the mixed gas. A valve 104 is opened periodically to connect the two sides of the transducer 98, and isolate it from the high pressure side of the screen 96, to permit the transducer 98 to be zeroed. The gas flowing from the flow rate sensor 92 enters the manifold 31 through which it flows to the gas conditioner subsystem 26. The pressure in the manifold 31 is sensed by a pressure transducer 106.

The manifold 31 is provided with two further safety switches. A subambient relief valve 108 opens if the pressure within the manifold 31 becomes less than ambient air pressure for any reason, and permits outside air to flow into the manifold 31. A safety valve 110 operated by a safety pilot valve 216 permits outside air to flow into the manifold 31 under three conditions. The valve 110 is operated if the system is off or there is a malfunction that cuts off the pressurized gas or electricity. Second, the valve 110 is operated if an overpressure in the manifold 31 is sensed. Third, the valve 110 acts as a pop-off valve when the pressure in the airway exceed a specified holding pressure. These conditions are activated by malfunction states that are not expected in normal operation, but must be accommodated should they occur. In the absence of such relief valves, the patient might be deprived of any gas or air for breathing, or the patient's lungs might be overpressurized. Provision of unpressurized air is preferable to such deprivation or overpressurization. Each condition is accompanied by a signal to the operator of the ventilator 20 that a malfunction is occurring, so that the operator may investigate and correct it.

A key feature of the pressurization/flow controller 30 is the rotary valves 76 and 78, that control the flow of oxygen and air, respectively, to the patient. Many gas flow controllers use feedback systems, which are relatively expensive. The valves 76 and 78 are not feedback or closed loop valves, but instead are individually calibrated and periodically zeroed to ensure their correct operation. The two valves 76 and 78 operate substantially identically, and therefore only the oxygen valve 76 will be described in detail.

Figure 3:
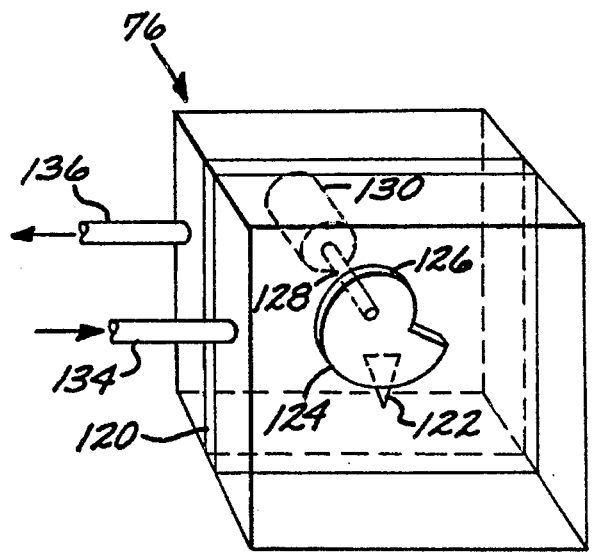
FIG. 3 is a schematic perspective cutaway view of a rotary gas flow control valve.

As depicted in FIG. 3, the valve 76 includes a stationary plate 120 having a triangular opening 122 therethrough. A movable disk 124 having a cam-shaped outer periphery 126 lies adjacent to and in contact with the stationary plate 120, to partially cover the opening 122. The movable plate 124 rotates on a shaft 128 in the center thereof, driven by a stepper motor 130. The stepper motor 130 of the preferred embodiment has about 0.45 degrees of rotation per step. The position of the disk 124 is determined by counting steps from the zeroed position. With each step, the coverage of the opening 122 changes slightly, so that either more or less gas is permitted to pass through the opening 122. A gas inlet line 134 to the valve 76 is on one side of the stationary plate 120, and a gas outlet line 136 from the valve 76 is on the other side of the stationary plate 120. The gas inlet line 134 is pressurized, and that pressure forces the gas through the opening 122 with a flow rate that depends upon the coverage of the opening 122 by the movable disk 124.

This type of valve 76 is highly reliable in its operation, amenable to computer control due to its digital stepping nature, fast acting, and has a high resolution. Because of the low pressures and flow rates of the gas and the large number of control steps, even normal variations in dimensions or operation of the valve 76, due to manufacturing tolerances, can lead to slight differences in the performance of each valve.

A calibration and rezeroing procedure is used to obviate these normal variations in operation of each valve. When each valve is manufactured, it is individually calibrated to establish a quantitative relationship between gas flow rate at a specified pressure (typically about 7 psig) and degree of rotation (as measured by counting the number of motor steps) of the movable disk 124 from a fully closed zero point. This calibration is prepared in the form of normalized values that can be used for any pressure drop, arranged in a table, and stored in the controller 28 in computer memory. When the ventilator 20 is in operation, the movable disk 124 is rotated to the fully closed position on a periodic basis (every eight breaths in the preferred embodiment) to establish the number of the motor step that corresponds to the fully closed position. The updated zero point is then used in conjunction with the calibration to calculate the rotary position required to provide a selected gas flow.

Figure 4:
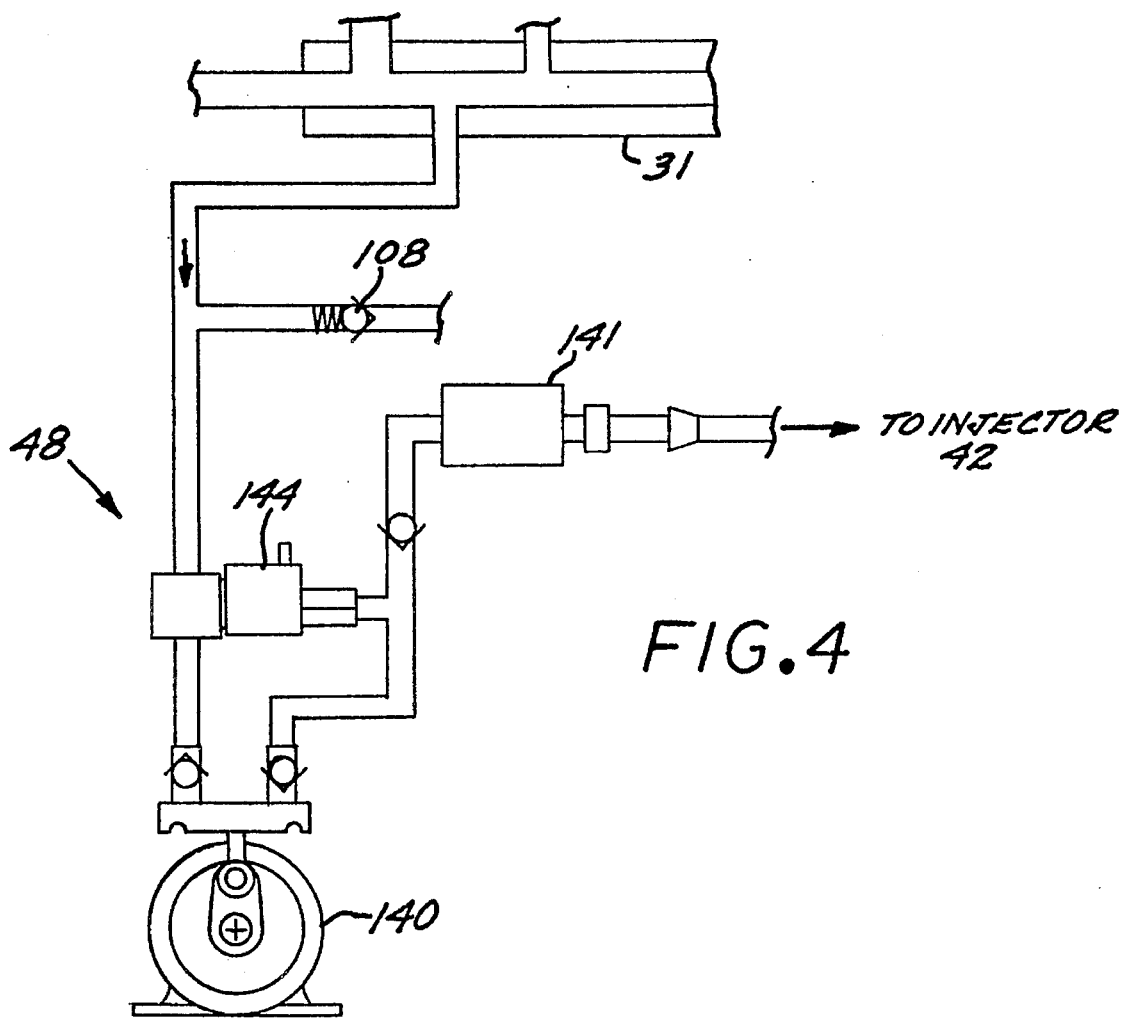
FIG. 4 is a block diagram of the nebulizer subsystem.

The nebulizer 48 is illustrated in FIG. 4. The nebulizer is a device for injecting controlled amounts of medication, such as for example a decongestant, directly into the respiratory tract of the patient. A nebulizer pump 140 receives a flow of the same mixture of oxygen and air breathed by the patient from the manifold 31, and pressurizes it to about 8–10 psi pressure. The gas is pumped through a filter 141 that removes particles smaller than about 0.3 micrometers, and to the nebulizer injector 42, where medication is mixed into the gas stream. In the event that a subambient condition occurs within the system, the pump 140 receives outside air through the valve 108 and continues to pump the air to the nebulizer injector. A nebulizer safety valve 144 has two states, one where the input side of the pump 140 is connected to the output side to prevent pressurized gas flow to the nebulizer, and the other where the gas flow is through the pump 140. The valve 144 normally operates in the second state so that the pump 140 forces gas to the nebulizer injector 42, allowing nebulization at low flow rates while still maintaining accurate blending. The valve 144 may be periodically switched to the first state to prevent too high a flow rate to the nebulizer injector 42, or to prevent drawing a vacuum on the manifold 31.

Figure 5:
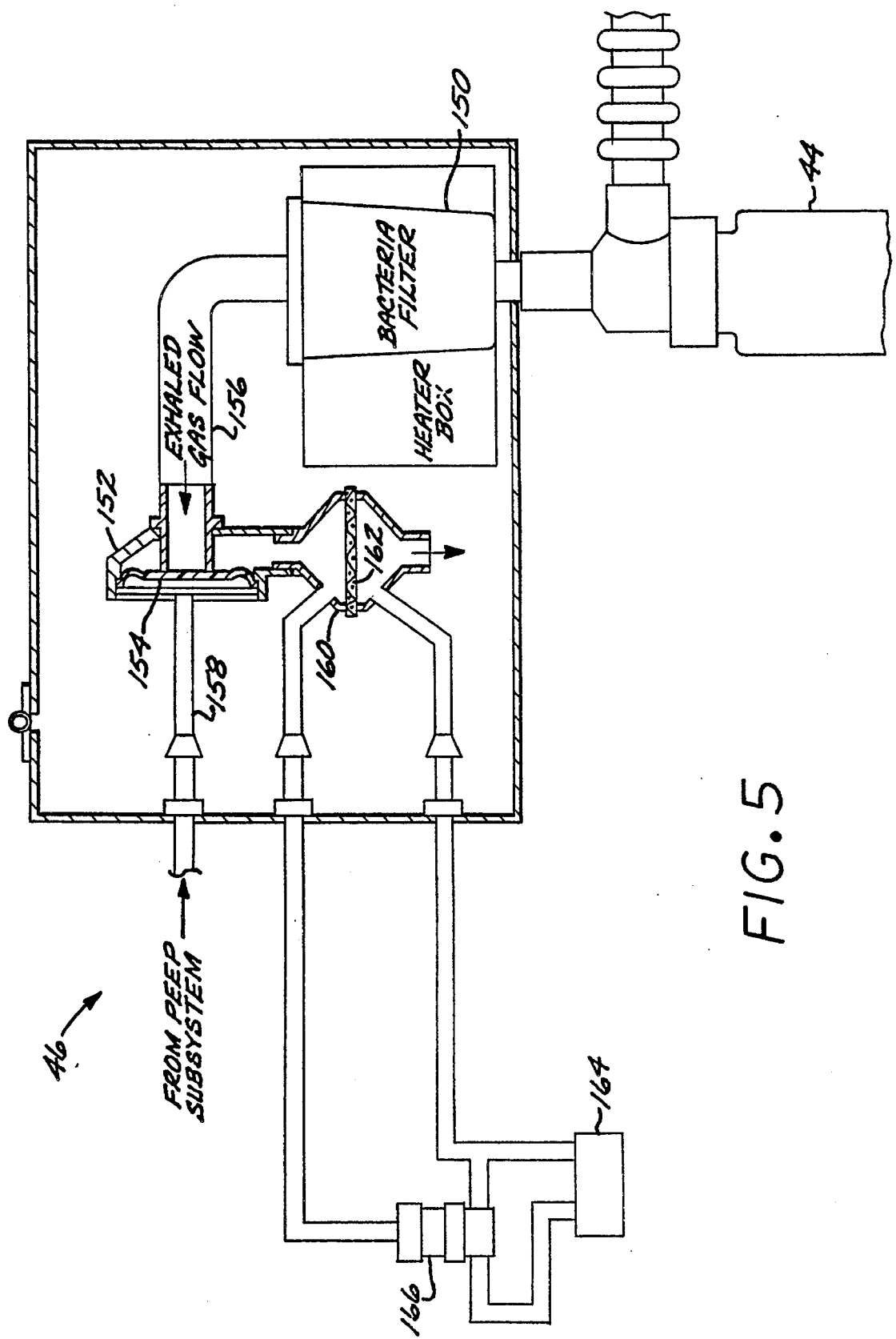
FIG. 5 is a block diagram of the exhalation subsystem.

The exhalation subsystem 46 is illustrated in FIG. 5. The exhaled gas from the patient first passes through the water trap 44 to drain the tubing leading from the patient. The gas is then filtered with a heated bacteria filter 150, which preferably removes particles of less than about 0.3 micrometer, to prevent bacteria exhaled by the patient from being introduced into the ambient air and to prevent contamination of the exhalation subsystem 46. Such bacteria filters are known in the art.

The filtered gas passes through an exhalation valve 152 which carries the gas from the filter 150. When a diaphragm 154 in the valve 152 is fully flexed to the right in the view of FIG. 5, the inlet line 156 is closed by the diaphragm 154 and no gas can flow therethrough. As the diaphragm 154 flexes to the left in the view of FIG. 5, an inlet line 156 becomes progressively more opened so that the gas therein can flow more freely. By moving the diaphragm 154 to the left or right, the resistance to the flow of exhaled gas in the line 156 is controlled. Thus, for example, if the therapist wishes to maintain the patient's lungs inflated at the end of a breath, the diaphragm 154 and the valve 152 are closed at the end of the breath so that the last portion of the exhaled gas is retained in the lungs of the patient.

The flexure of the diaphragm 154 is controlled by pressurizing the back side of the diaphragm 154 through a diaphragm control line 158. The opening against which the diaphragm 154 seats has a precisely dimensioned diameter to produce a well-defined force of area times pressure against the right-hand side of the diaphragm. The force against the left-hand side of the diaphragm 154 is determined by its area times the pressure against the left-hand side. To maintain a force equilibrium, the pressure against the left-hand side is varied through the control line 158 by the PEEP subsystem, in the manner to be discussed subsequently.

The air passing through the valve 152 next flows through an exhalation flow sensor 160. The sensor 160 functions in the same manner as the inhalation flow rate sensor 92. The exhaled gas passes through a acre en 162, which causes a pressure drop. The pressure in the sensor 160 is measured upstream of the screen 162 and downstream of the screen 162 by a differential pressure transducer 164, and the pressure difference related to the gas flow rate. A zeroing valve 166 is periodically operated to connect the high pressure side and the low pressure side of the transducer 164, so that it may be zeroed. In normal operation, the valve 166 connects the high pressure side of the transducer 164 to the high pressure side of the screen 162. The gas leaving the exhalation flow sensor 160 is released to the atmosphere.

Figure 6:
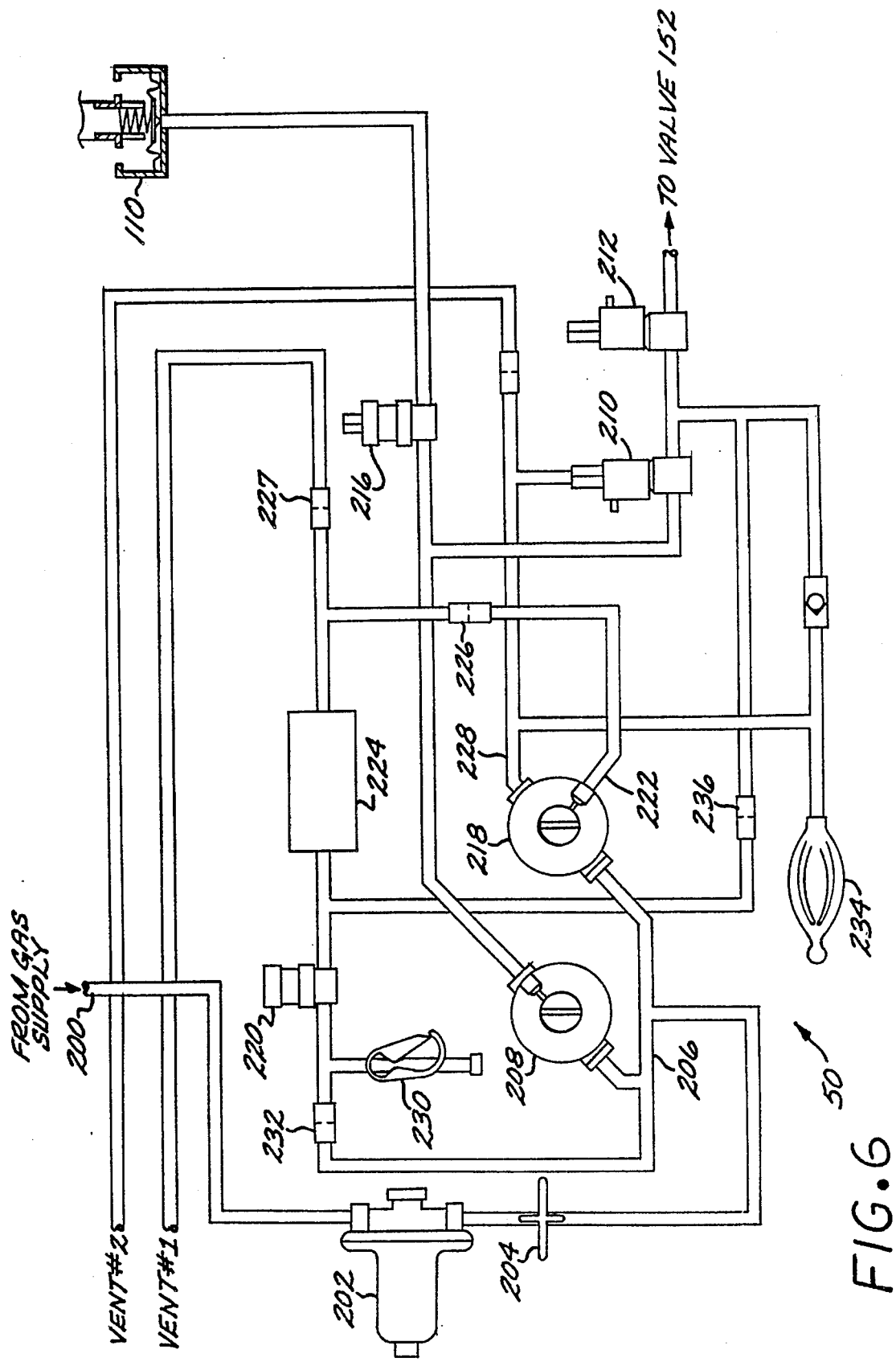
FIG. 6 is a block diagram of the PEEP subsystem.

The PEEP subsystem 50, illustrated in FIG. 6, controls the pressure on the back side of the diaphragm 154 of the exhalation valve 152. The PEEP subsystem 50 has two important functions. First, during inspiration of the patient, the exhalation valve 152 must be held firmly closed, so that the air flow from the pressurization/flow controller 30 flows into the patient and not out through the exhalation system 46. Second, during expiration of air by the patient, the valve 152 is opened during part of the expiration period but may be closed or partially closed toward the end of the expiration period to maintain pressure in the patient's lungs. Because of the pressure cycling and accumulation requirements of the PEEP subsystem, the first and second functions are performed by different but interrelated parts of the PEEP subsystem.

Pressurized gas is supplied to the PEEP subsystem 50 through a line 200 from the pressurization/flow controller 30. The pressure of the gas is regulated by a regulator 202 to a pressure of about 5–7 psig, and filtered by a filter 204 that removes particles larger in size than about 0.3 micrometers. The filtered, regulated gas enters a manifold 206 from which various components of the subsystem 50 are supplied.

The first subsystem function, closure of the exhalation valve 152 during inspiration of gas into the patient, is accomplished by connecting the backside of the diaphragm 154 to an IMV regulator 208 through an exhalation pi lot valve 210. The diaphragm 154 is held closed, so that air flows from the pressurization/flow control subsystem 30 into the patient. A safety valve 212 is placed between the exhalation pilot valve 210 and the exhalation valve 152, so that, if there is an equipment malfunction such as an equipment-caused overpressure, the backside of the diaphragm 154 can be vented to atmosphere to maintain the exhalation valve 152 in an opened state.

Other situations involving abnormally high pressures can also occur, as when the patient coughs. In that event, the valve 212 operates to vent to atmospheric pressure, thereby reducing the pressure on the back side of the diaphragm 154 to atmospheric and opening the exhalation valve 152. The abnormally high pressure created by the patient is thereby vented, even though the system is inspirating at the time of the cough.

During exhalation of gas by the patient, the valve 152 is controlled by the PEEP subsystem 50 to maintain a therapist-selected minimum baseline pressure in the airway. Again, the control is achieved by applying a backside pressure to the diaphragm 154 of the exhalation valve 152, not by directly forcing gas into the airway. The backside pressurizing gas is supplied by a PEEP regulator 218 through the pilot valve 210, which switches between regulators 208 and 218 during inspiration and exhalation portions of the breath, respectively.

When a PEEP setting is selected by the therapist, a PEEP pressure control valve 220 is pulsed at a preselected duty cycle to produce an appropriate pressure at the inlet of the dome diaphragm 222 of the PEEP regulator 218. The connection to the regulating diaphragm 222 occurs through an accumulator 224 and in conjunction with flow restrictors 226 and 227 to reduce the magnitude of the pulsations that could otherwise be transmitted to the diaphragm 154.

The PEEP pressure control valve 220 does not produce sufficiently high flow volumes to operate the large diaphragm 154 at the speeds typically required, and the PEEP regulator 218 acts as an amplifier of the pressure signal produced by the valve 220. The dome pressure 222 of the regulator 218 controls the pressure in the output line 228 of the regulator 218, and thence the pressure applied to the backside of the diaphragm 154. The pressure on the diaphragm 154, and thence the baseline pressure in the airway 52 between breaths, is thereby controlled by changing the duty cycle of the PEEP pressure control valve 220.

The exhalation valve 152 could be operated with the arrangement just described, but would not produce the most preferred performance, for the following reason. The pressure output of the regulator 218 varies nonlinearly with the gas flow rate to the dome diaphragm 222, and therefore the pressure applied to the diaphragm 154 of the exhalation valve 152 varies nonlinearly with duty cycle of the valve 220. A modification to the system causes the pressure applied to the exhalation valve 152 to vary more linearly with the duty cycle of the valve 220. This approach is open loop for safety, but with minor servo action for accuracy.

The output flow of the valve 220 is shaped to achieve more nearly linear performance by providing a variable accumulator 230 upstream of the PEEP pressure control valve 220. The variable accumulator 230 is a chamber whose volume is controllably varied, depending upon the pressure requirements on the output of the valve 220. A flow restrictor 232 upstream of the valve 220 and the variable accumulator 230 limits the flow through the valve 220 when the valve is open, and determines the time required to refill the accumulator 230 when the valve 220 is closed. When the valve 220 opens, the flow through the valve 220 is initially high as the variable accumulator 230 exhausts quickly, then reduces to a steady flow dictated by the inlet restrictor 226 and the pressure setting of the regulator 202. When the valve 220 closes, the variable accumulator 230 begins charging for the next cycle.

For "low" duty cycles where the "on" time of the valve 220 is short (i.e., the valve 220 is open for a small fraction of the time), there is a high flow rate through the valve 220 because of the rapid discharge of the variable accumulator 230. An increase in the "on" time significantly increases the average flow rate. For "high" duty cycles, increasing the "on" time by a small amount adds only marginally to the average flow rate, because the variable accumulator is nearly exhausted after a long period of outflow. A high duty cycle results in incomplete filling of the accumulator 230, further decreasing the average flow rate. Increasing the volume of the variable accumulator 230 magnifies this effect, and is used to boost flow at low duty cycles. The volume of the accumulator 230 has little effect on the steady flow reached after long "on" times, because this flow is a function of the pressure upstream of the inlet restrictor 232. The regulator 202 is adjusted to determine the upstream pressure in the manifold 206 with the valve 220 at a 100 percent duty cycle, fixing the high end of the scale. The variable accumulator 230 is then adjusted to calibrate the circuit at low duty cycles without affecting the high end adjustment.

An accumulator bag 234 supplements the output air flow of the regulator 218 after exhalation, thereby rapid repressurizing the backside of the diaphragm 154 to the pressure level required by the PEEP setting. This rapid repressurization prevents undershooting of the PEEP pressure immediately after exhalation. A flow restrictor 236 causes slight overfilling of the accumulator bag 234 during inspiration to further insure that no PEEP pressure undershooting can occur when the backside of the diaphragm 154 is refilled.

Figure 7:
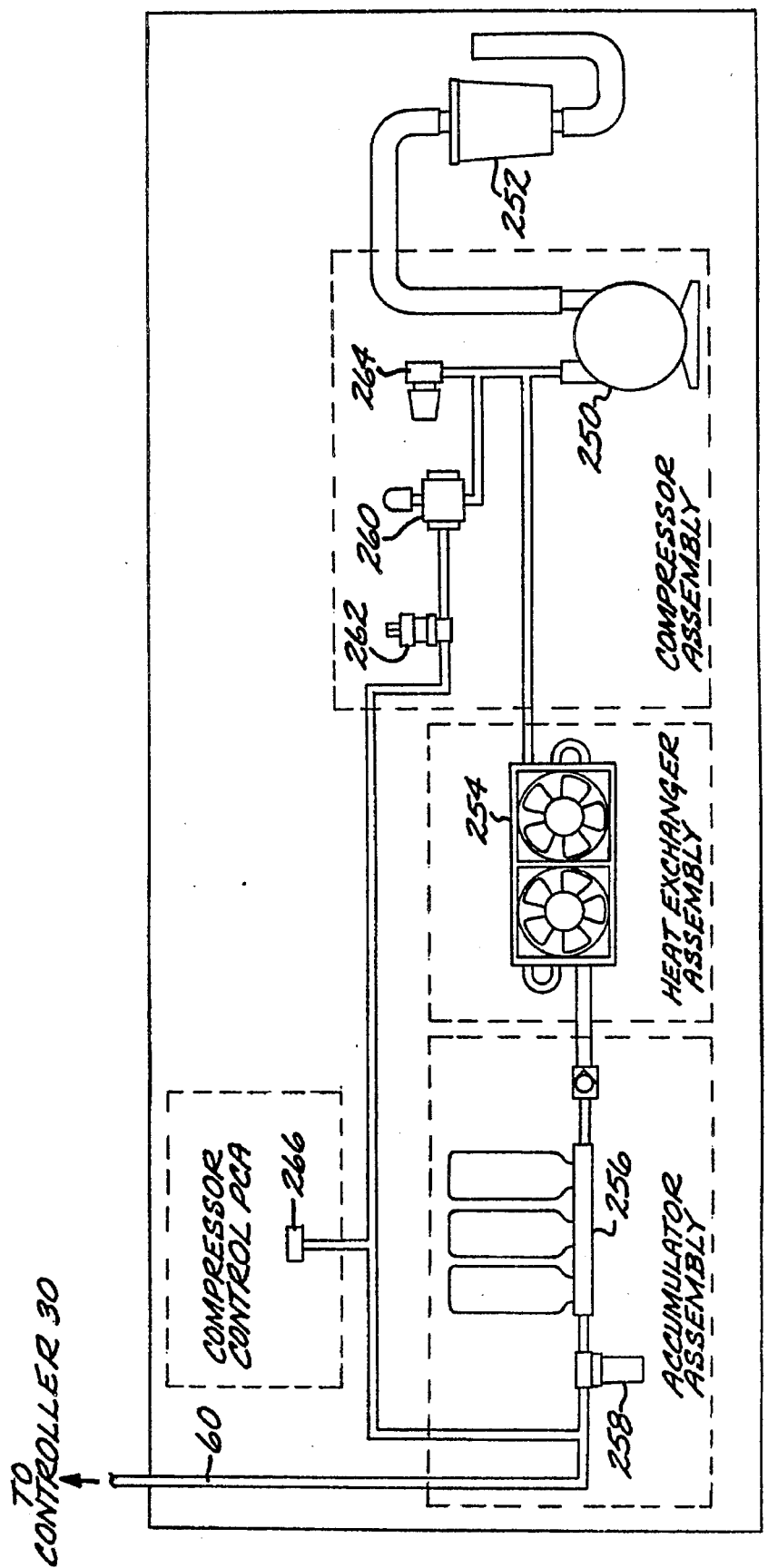
FIG. 7 is a block diagram of the compressor subsystem.

The compressor subsystem 24 is illustrated in FIG. 7. A compressor 250 draws in air through a filter 252, and compresses the air. The compressed air is cooled by a heat exchanger 254 to condense moisture and then stored in an accumulator 256. When there is a demand from the pressurization/flow controller 30, compressed air flows out of the accumulator 256 through the line 60. The compressed air passes through a water trap 258 to remove any moisture that may have condensed.

The maximum pressure of the accumulator 256 is established by a controllable compressor unloading valve 260 that communicates with the output of the compressor 250. The compressor unloading valve 260 has a silencer thereon to reduce the noise level in the ambient environment. The release pressure sensed by a pressure transducer 266 is used by the controller 28 to control a compressor unloading pilot valve 262, which in turn controls the compressor unloading valve 260.

To ensure that the system cannot overpressurize, a manual pressure relief valve 264 communicates with the output of the compressor 250, so that the pressurized air in the accumulator 256 cannot exceed the pressure set on the relief valve 264. In a preferred embodiment, the pressure relief valve 260 is set to about 40 psig. A pressure sensor 266 measures the pressure downstream of the accumulator 256.

The accumulator 256 and compressor 250 are together sized so that the amount of air available is sufficient to meet demand needs for the ventilation of a patient, with the compressor 250 operating continuously. The inclusion of the accumulator in the system reduces the maximum flow rate of air that must be supplied by the compressor to meet patient needs during inhalation. The compressor may therefore be made smaller and quieter than would be the case in the absence of the accumulator. In a preferred embodiment, the usable volume of the accumulator 256 is about 12 liters, and the compressor 250 is a Thomas Industries 2619 Series, rated at 2.95 standard cubic feet per minute of air flow at 15 psig (pounds per square inch, gauge) or greater pressures. This compressor has a noise level of 60 decibels (db), while a compressor sized to meet maximum load would have a considerably greater noise level.

Figure 8:
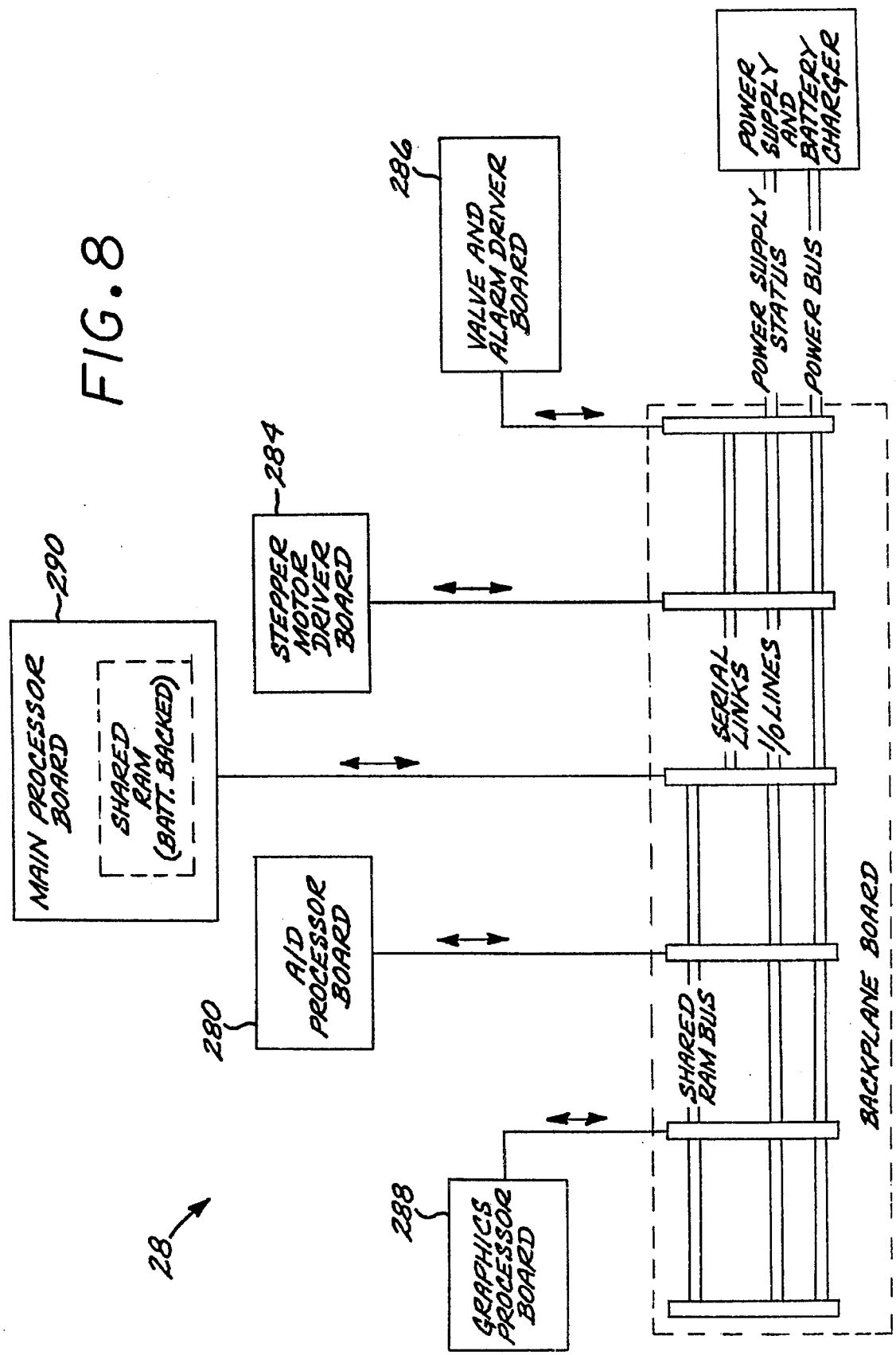
FIG. 8 is a block diagram of the controller subsystem.

The controller subsystem 28 is illustrated in FIG. 8. In the preferred approach, the controller 28 includes four microprocessor that monitor and/or control various aspects of the individual subsystems, and a main microprocessor that integrates the operations of the other microprocessors. This approach permits the most efficient use of the electronic components, and avoids unnecessarily complex interactive computer programming that might be necessary if all functions were packed into a single microprocessor. Their programming is provided by EPROMs (Erasable Programmable Read Only Memories) that can be externally programmed and duplicated, and then inserted into the microprocessor boards.

An A/D (analog to digital) microprocessor 280 receives the analog signals from the various pressure transducers described previously, such as transducers 54, 82, 83, 98, 106, and 164, and any others that might subsequently be added to the system. These signals are digitized, in the preferred embodiment into 8 bit words, and conveyed to a shared RAM bus 282.

A stepper motor driver microprocessor 284 controls the stepper motors 76 and 78, according to the principles set forth previously herein. A Valve and Alarm Driver Board 286 controls the various open/close type solenoid valves described previously, such as the valves 88, 104, 144, 166, 210, 212, 216, 220, and 263, the nebulizer pump 140, and displays and alarms that convey information to the user of the ventilator 20.

A graphics microprocessor 288 is programmed to handle most of the operator input and operator display functions, according to a process to be described subsequently.

A main microprocessor 290 includes a battery-backed, shared RAM (random access memory) that is accessible to all of the other microprocessors, and performs integration functions according to the procedures discussed previously.

Figure 9:
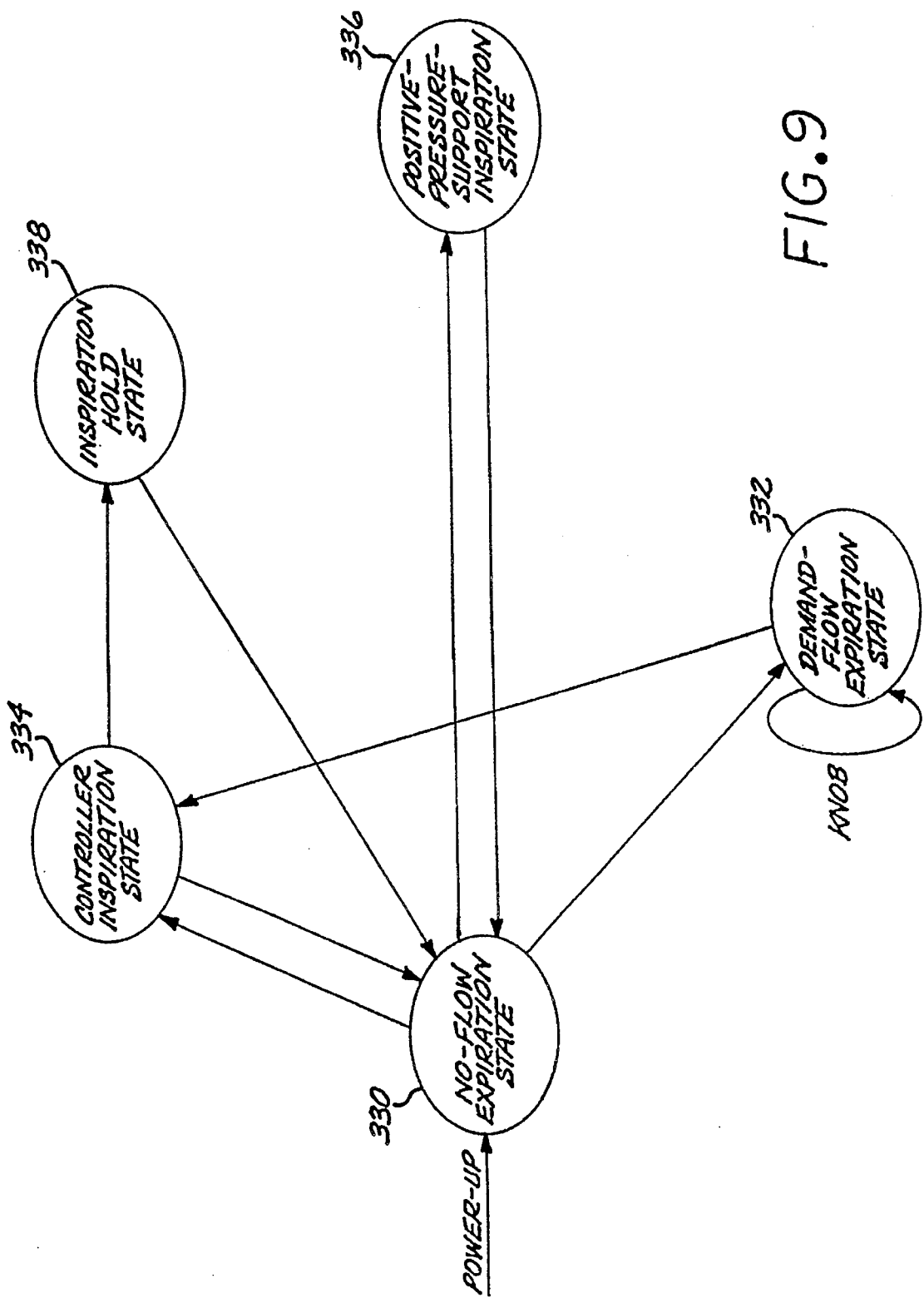
FIG. 9 is a state machine diagram for the ventilator system.
Figure 10:
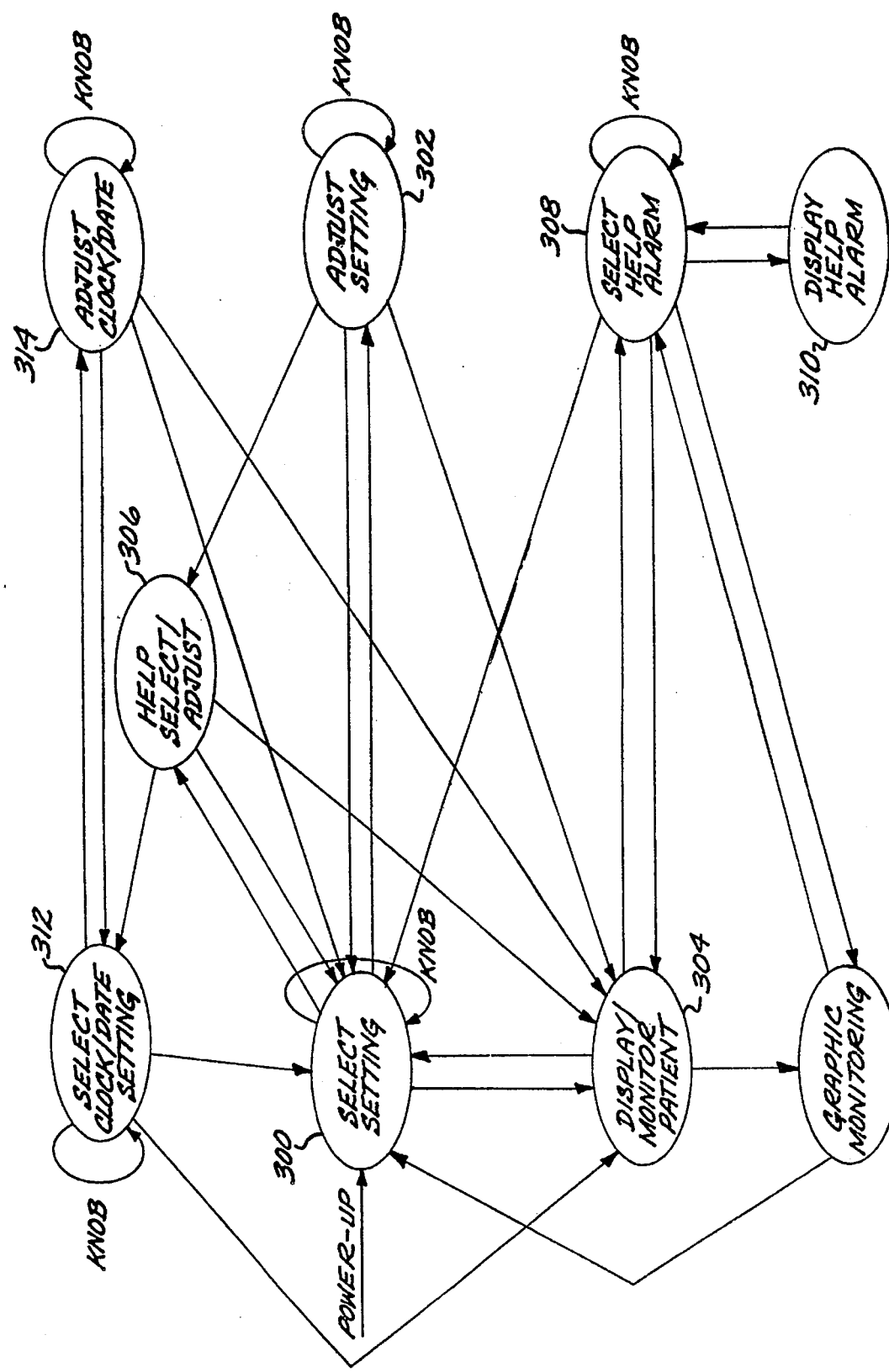
FIG. 10 is a state diagram for the graphics interface.

The various microprocessors operate according to instruction sets, and using data, provided in EPROMs. The processes can be represented by state diagrams, from which detail code is written by those knowledgeable in microprocessor programming. FIG. 9 is a state machine diagram for the ventilator control functions, and FIG. 10 is a state diagram for the user interface. States are represented by "balloons", and arrows represent transitions between states permitted by the microprocessor programming of the presently preferred embodiment. An important virtue of the present microprocessor-controlled ventilator, the state-programming approach, and the use of programming stored on EPROMs is that the states and the transitions can be readily modified. For example, if a new philosophy of respiratory therapy is developed or if a therapist requires some new or unusual procedure for a particular patient or condition, the existing states and transitions can be modified, the programming modified and burned into an EPROM, and the new capability supplied to all or some of the ventilators in use simply by replacing the appropriate EPROM.

The various ventilation functions can be represented as the five states depicted in FIG. 9. The appropriate state, or sequence of states, is selected responsive to the profile selected by the therapist. A no-flow expiration state 330 is that prior to or between breaths. A demand-flow expiration state 332 is selected if the ventilator is operated to follow and assist fully spontaneous patient breathing. That is, the therapist may determine that the patient requires assistance in spontaneous breathing, and the ventilator follows the breathing of the patient to provide a particular mix of gases, a higher inspiration pressure, or positive end expiratory pressure, for example. At the opposite end of the spectrum is a controlled inspiration state 334, where the ventilator supplies a breath without any assistance or effort by the patient. The therapist may select ventilator operation solely in the demand-flow expiration state 332, solely in the controlled inspiration state 334, or a combination of the two. In the latter case, known as synchronous intermittent mandatory ventilation (SIMV), the operation of the ventilator may be viewed as a sequential transition from state 330 to state 332 for a patient breath, then a transition to state 334 for a machine inspiration, and finally a transition back to state 330 until either the patient takes another spontaneous breath (state 332) or the ventilator determines that another machine-driven inspiration is required (state 334). In each of the states 332 and 334, the operation of the machine such as gas mixture, pressures, volumes, times, nebulization, etc. is fully controllable by the therapist in the manner to be discussed in relation to FIG. 10.

A Positive-Pressure-Support state 336 permits the pressure in the lungs of the patient to be raised when the patient draws a breath. An inspiration hold state 338 is reached from the controlled inspiration state 334, and provides the capability for the gas introduced during a machine breath to be held inside the patient for a period of time, after which the breath is released and the system returns to the no-flow expiration state 330.

The presently preferred microprocessor programming of these states and transitions is presented in Appendix A, which is attached hereto and made a part hereof.

The present ventilator therefore is highly versatile, in that it offers a wide assortment of options and sequences from which the therapist may choose precisely the correct combination of respiratory therapy for a situation. This versatility, however, creates the need for a readily understood and applied selection and monitoring approach, so that the therapist can readily select the desired combination of states and conditions for each state and then monitor the functioning of the ventilation activity.

To implement the control and monitoring functions, the present apparatus uses a single cathode ray tube (CRT) to display all visual information to the therapist, and as the vehicle for changing control parameters of the ventilator. In the preferred approach, most display information is presented on one screen of information termed the "Display" screen, and control parameter information is displayed and made changeable on another screen of information, termed the "Control" screen. That is, the user of the system can switch the single screen between two different presentations, one of which presents patient and system operating data, and the other of which permits the changing of system operating parameters.

When the Control screen is viewed, all control functions to be accomplished with one control knob 296 and one "enter" switch 298, a procedure implemented with well-known "mouse"-type technology. Optionally but preferably, two additional switches, one to change screens and the other to request help, are provided.

The relative simplicity of this approach is to be contrasted with the complexity of prior approaches, wherein information is displayed on a myriad of different meters and screens, and a variety of different controls must be manipulated to control the system. It is not easy to monitor patient functions and make control changes in the relative quiet of a controlled situation using the prior approach, but in the noise and haste of a hospital emergency setting there is a much greater chance of error than when the present approach is used. Moreover, the microprocessor/EPROM technique of the present invention, when coupled with the concentration of display and control functions on a single screen, permits reprogramming and custom tailoring ventilator systems as needed.

FIG. 10 is a state diagram of the user interface for controlling the ventilator. This state diagram is interpreted by recognizing that the interface is in one of the states illustrated by the "bubbles", and then considering the options available. For example, when the interface is in the "Select Setting" state 300, the user may select any of several options, indicated by arrows extending out of the state 300. The user may manipulate the control knob 296 to select a function to be controlled, such as, for example, tidal volume, peak pressure, etc., whose current values are displayed. If the user then presses the enter switch 298, the state of the interface changes to an "Adjust Setting" state 302, and the selected quantity may be varied by turning the control knob 296 until the desired value is reached. Pressing the enter switch 298 again returns the interface to the select setting state 300, and establishes the manipulated setting in the microprocessor through the shared RAM.

The only other options available to the user in the Select Setting state 300 are to press the screen change switch or the help switch, where provided. The screen change switch causes a CRT 58 to exhibit the Display screen, state 304, rather than the Control Screen. The help switch causes a listing of common problems or questions, and their solutions or answers, to be displayed, state 306. By combining these four functions (control knob, enter switch, help switch, and screen change switch) in various ways, the user can accomplish the great majority of control and display operations required to use the system.

A second set of help information is available from the display state 304 by pressing the help switch. The Select Help Alarm state 308 is entered, wherein the user can select how alarms are to be displayed, state 310.

Finally, from the help state 306, the user can select the date/clock to be changed, state 312, by pressing the enter switch twice in one second. By pressing the enter switch again, the clock and date can be changed with the control knob, state 314. Since clock and date adjustments occur relatively rarely and not as a part of day-to-day patient care, this state is intentionally difficult to reach.

As indicated, based upon these state diagrams, software coding is within the skill of those in the art. Manipulation of the control knob to select and/or display on-screen icons or numbers is a well known software technique. The interpretation of switch movements in various states also is readily accomplished. The presently preferred microprocessor programming for the interface is presented in Appendix B, which is attached hereto and made a part hereof.

Figure 11:
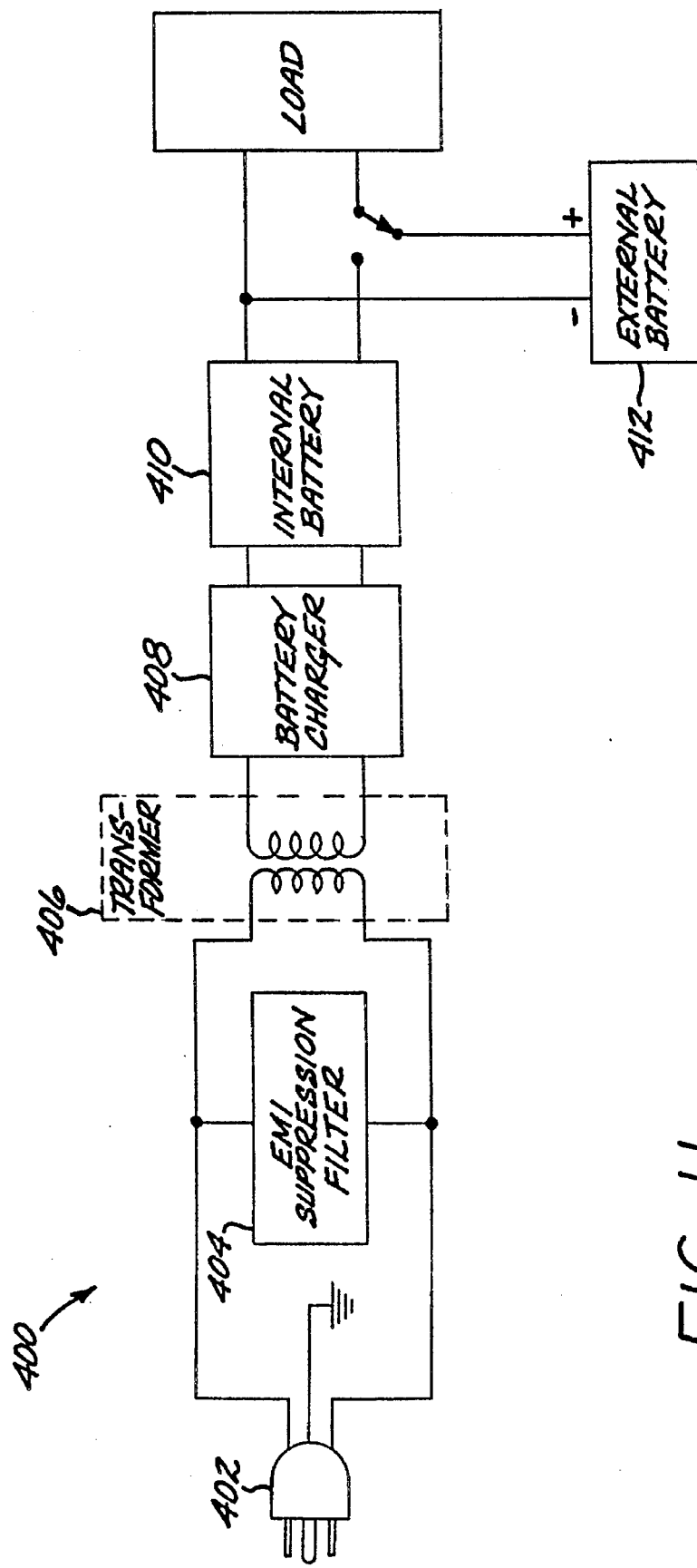
FIG. 11 is a block diagram for the power supply of the ventilator.

Electrical noise and power interruptions are of concern in a ventilator system that is supplying aeration to a patient. Most hospitals have backup power that is activated shortly after a power outage, but that power is initially so irregular that even short interruptions may interfere with monitoring and control circuitry. A preferred power supply 400 for the present invention is depicted in FIG. 11. The power for the ventilator 20 is taken from an available 120 volt, 60 Hz wall receptacle through a plug 402. An electromagnetic suppression filter 404 is applied across the active leads.

The 120 volt power is passed through a power transformer 406 and supplied to a battery charger 408. The battery charger 408 charges an internal 12 volt battery 410, and, optionally, an external 12 volt battery 412. The ventilator power requirements, including the electronics, are supplied as 12 volt DC current. This arrangement avoids the great part of interference on the power lines, as well as provides a backup power supply that permits the ventilator to run without any external power for at least several minutes until another stable source of AC power is established.

The present invention thus provides an important advance in the art of human lung ventilator systems, both in capability and ease of use. Although particular embodiments of the invention have been described in detail for purposes of illustration, various modifications may be made without departing from the spirit and scope of the invention. Accordingly, the invention is not to be limited except as by the appended claims.

What is claimed is:

1. A ventilator system for use in assisting a patient to breathe, comprising:

gas control means for mixing and regulating the gas that is to flow to a patient and receiving the gas that flows from the patient, the gas control means including flow control means for mixing together controllable amounts of two gases to form a mixed gas that flows to the patient, the flow control means including a separate, independently controllable custom-calibrated rotary flow control valve for each of the two gases; and controller means for independently controlling the two rotary flow control valves, wherein the controller means includes a calibration table for each of the rotary flow control valves, the calibration table including a correlation of gas flow rate as a function of rotary flow control valve position relative to a rotary flow control valve zero flow position, and means for automatically and periodically determining the rotary flow control valve zero flow position corresponding to a zero flow of each of the rotary flow control valves.

2. The ventilator system of claim 1, wherein each of the rotary flow control valves includes a plate having an opening therethrough, a movable disk having a cam-shaped surface, the disk being disposed in proximity to the plate so that the cam-shaped surface covers a controllable portion of the opening in the plate as the disk is rotated, and a motor that rotatably and controllably drives the movable disk.

3. The ventilator system of claim 2, wherein the controller means includes means for periodically closing the rotary valve to a fully closed position to establish a zero rotation position.

4. A ventilator system for use in assisting a patient to breathe, comprising:

gas control means for mixing and regulating the gas that is to flow to a patient and receiving the gas that flows from the patient, the gas control means including flow control means for mixing together controllable amounts of two gases to form a mixed gas that flows to the patient, the flow control means including a separate, independently controllable custom-calibrated rotary flow control valve for each of the two gases, ventilation tube means extending to the patient for conducting the mixed gas to the patient and for receiving exhaled gas from the patient, and positive end expiration pressure means for controllably maintaining a minimum pressure in the exhaled gas; and controller means for independently controlling the two rotary flow control valves, wherein the controller means includes a calibration table for each of the rotary flow control valves, the calibration table including a correlation of gas flow rate as a function of rotary flow control valve position relative to a rotary flow control valve zero flow position, and means for automatically and periodically determining the rotary flow control valve zero flow position corresponding to a zero flow of each of the rotary flow control valves.

5. The ventilator system of claim 4, wherein each of the rotary valves is driven by a stepper motor.

6. The ventilator system of claim 4, wherein the gas control means further includes an inhalation flow sensor having a screen through which the mixed gas flows and a pressure sensor that senses the pressure drop across the screen, whereby the mixed gas flow rate is determined with a preexisting calibration relationship.

7. The ventilator system of claim 4, wherein the gas control means further includes a nebulizer that injects a controllable flow of a third component into the mixed gas stream.

8. The ventilator system of claim 4, wherein the ventilation tube means includes a filter for the mixed gas, a humidifier for the mixed gas, a water trap for the exhaled gas, and a heated filter for the exhaled gas.

9. The ventilator system of claim 4, further including compressor means for supplying compressed gas to the gas control means, in the event that an external supply of compressed gas is not available.

10. The ventilator system of claim 9, wherein the compressor means includes a compressor that operates continuously against a compressor accumulator and is sized to meet average rather than peak gas flow volume.

11. The ventilator system of claim 4, wherein the controller means includes an operator interface having a cathode ray tube, and wherein the controller means further includes means for displaying to an operator patient and ventilator parameters, and operator control options on the cathode ray tube.

12. The ventilator system of claim 4, wherein the controller means includes an operator interface having a single control knob for selecting ventilator control modes and parameter settings.

* * * * *